(12) United States Patent
Elmaleh (10) Patent No.: US 10,300,154 B2
(45) Date of Patent: May 28, 2019

(54) ANTICOAGULANT DERIVATIVES FOR CARDIOVASCULAR IMAGING

(71) Applicant: David R Elmaleh, Newton, MA (US)

(72) Inventor: David R Elmaleh, Newton, MA (US)

(*) Notice: Subject to any disclaimer, the term of this patent is extended or adjusted under 35 U.S.C. 154(b) by 0 days.

(21) Appl. No.: 15/511,848

(22) PCT Filed: Sep. 17, 2015

(86) PCT No.: PCT/US2015/050781
§ 371 (c)(1),
(2) Date: Mar. 16, 2017

(87) PCT Pub. No.: WO2016/044645
PCT Pub. Date: Mar. 24, 2016

(65) Prior Publication Data
US 2017/0290931 A1 Oct. 12, 2017

Related U.S. Application Data

(60) Provisional application No. 62/051,522, filed on Sep. 17, 2014.

(51) Int. Cl.
*A61K 51/00* (2006.01)
*A61M 36/14* (2006.01)
*A61K 51/04* (2006.01)
*G01N 33/68* (2006.01)
*A61K 9/00* (2006.01)

(52) U.S. Cl.
CPC ........ *A61K 51/0453* (2013.01); *A61K 9/0019* (2013.01); *G01N 33/6893* (2013.01); *G01N 2800/32* (2013.01)

(58) Field of Classification Search
CPC ............. A61K 51/0453; A61K 9/0019; G01N 33/6893; G01N 2800/32
USPC .......................................................... 424/1.89
See application file for complete search history.

(56) References Cited

U.S. PATENT DOCUMENTS

| | | | |
|---|---|---|---|
| 5,434,150 A | 7/1995 | Austel et al. | |
| 6,087,380 A * | 7/2000 | Hauel ................. | C07D 209/14 514/336 |
| 2010/0111864 A1* | 5/2010 | Ametamey ........ | A61K 51/0459 424/1.89 |
| 2011/0065682 A1 | 3/2011 | Clasby et al. | |
| 2011/0196383 A1 | 8/2011 | Aziz et al. | |
| 2012/0028901 A1 | 2/2012 | Dockal et al. | |
| 2012/0202232 A1 | 8/2012 | Braun et al. | |
| 2013/0289248 A1 | 10/2013 | Van Ryn et al. | |

FOREIGN PATENT DOCUMENTS

WO   WO 2013/168025   11/2013

OTHER PUBLICATIONS

Jaffer et al. Cir. Res. 2004; 94, 433-445.*
Sinzinger et al. Eur. J. Nucl. Med. (1986) 12: 291-292.*
International Search Report PCT/US15/50781 dated Dec. 17, 2015.

* cited by examiner

*Primary Examiner* — Michael G. Hartley
*Assistant Examiner* — Sean R Donohue
(74) *Attorney, Agent, or Firm* — Pearl Cohen Zedek Latzer Baratz LLP

(57) ABSTRACT

The invention provides cardiovascular imaging agents comprising an anticoagulant (e.g., dabigatran derivatives) with a label (e.g., radiolabeled, fluorinated or radiofluorinated). Methods for using the cardiovascular imaging agents and kits containing the cardiovascular imaging agents or components suitable for production of the cardiovascular imaging agents are also provided.

13 Claims, 2 Drawing Sheets

ANTICOAGULANT DERIVATIVES FOR CARDIOVASCULAR IMAGING

CROSS-REFERENCE TO RELATED APPLICATION

This application is a National Phase Application of PCT International Application PCT/US2015/050781, filed Sep. 17, 2015, which claims priority to and the benefit of U.S. Provisional Patent Application 62/051,522, filed Sep. 17, 2014, all of which are incorporated by reference herein in their entirety.

FIELD OF THE INVENTION

The invention relates to medical imaging for cardiovascular conditions. Specifically, the invention relates to anticoagulants and their derivatives, such as dabigatran derivatives (radiolabeled, fluorinated or radiofluorinated), and uses thereof for positron emission tomography (PET) and single photon emission computerized tomography (SPECT) imaging and related methods of diagnosis and treatment.

BACKGROUND OF THE INVENTION

According to the American Heart Association, heart disease, also called cardiovascular disease and coronary heart disease, is a simple term used to describe several problems related to plaque buildup in the walls of the arteries, or atherosclerosis. As the plaque builds up, the arteries narrow, making it more difficult for blood to flow and creating a risk for heart attack or stroke.

Atherosclerosis is a condition of hardening of the arteries, in which plaque builds up inside the arteries. Plaque is made of cholesterol, fatty substances, cellular waste products, calcium and fibrin (a clotting material in the blood). Plaque may partially or totally block the blood's flow through an artery in the heart, brain, pelvis, legs, arms or kidneys. Two things that can happen where plaque occurs include (1) a piece of the plaque may break off; and (2) a blood clot (thrombus) may form on the plaque's surface. Some of the diseases that may develop as a result of atherosclerosis include coronary heart disease, angina (chest pain), carotid artery disease, peripheral artery disease (PAD) and chronic kidney disease.

Arteriosclerosis is a leading cause of death in the Western countries. It is becoming increasingly clear that arteriosclerosis is an immuno-inflammatory process that involves complex interactions between the vessel wall and various blood components. The atherogenic process involves sequestration of partially oxidized lipids in the vessel wall that leads to endothelial injury. Endothelial alteration promotes adherence of mononuclear cells and platelets, which contribute to phenotypic transformation of medial smooth muscle cells from adult to embryonic forms. These transformed muscle cells proliferate and migrate to intima. Simultaneously, accumulation of lipids by monocytes leads to the formation to foam cells. The platelets, macrophages, and proliferating smooth muscle cells of atherosclerotic plaque provide important targets for the development of non-invasive diagnostic agents.

Several imaging modalities and molecular imaging techniques were used to image and characterize plaque. These imaging methods include some advancements in Intravascular ultrasound (IVUS), Optical Coherence Tomography (OCT), CT, near infrared spectroscopy molecular imaging, MR and MR molecular imaging and The standard technique for diagnosis of atherosclerotic lesions utilizes arteriography assessment and development of a non-invasive test is highly desirable. Such a test could be important not only for diagnosis but also for the development and monitoring of therapies directed at altering the natural history of these lesions. However, there are a limited number of reports describing non-invasive visualization of atherosclerotic lesions. These studies have targeted the thrombotic component overlying the atherosclerotic lesion (with radiolabeled fibrinogen), platelet aggregation at regions of turbulent flow (with labeled platelets or platelet-specific antibodies) or proteins likely to be incorporated into atherosclerotic lesions (with radiolabeled autologous lipoproteins). Nonspecific uptake of human IgG via Fc receptors of macrophages has also been used as the basis for a targeting strategy. Other methods developed monoclonal IgM antibody, Z2D3, which was initially developed with specificity for an antigen expressed by the proliferating smooth muscle cells of human atherosclerotic lesion and P2 targeting like Ap4A.

Coronary heart disease alone caused 1 of every 6 deaths in the United States in 2009. Each year, an estimated 635,000 Americans have a new coronary attack and 280,000 have a recurrent attack. It is estimated that an additional 150,000 silent first myocardial infarctions occur each year. Approximately every 34 seconds, 1 American has a coronary event, and approximately every 1 minute, an American will die of one.

The total number of inpatient cardiovascular operations and procedures increased 28%, from 5,939,000 in 2000 to 7,588,000 in 2010 (National Heart, Lung, and Blood Institute computation based on National Center for Health Statistics annual data). The total direct and indirect cost of CVD and stroke in the United States for 2009 is estimated to be $312.6 billion. This figure includes health expenditures (direct costs, which include the cost of physicians and other professionals, hospital services, prescribed medications, home health care, and other medical durables) and lost productivity that results from morbidity and premature mortality (indirect costs).

As one can appreciate, sensitive and specific agents are needed to identify the early stages of plaque and thrombus formation to save lives and reduce burden on the current medical system.

Clinical imaging technology plays a significant role in diagnosis and prognosis of heart diseases. Some of the radiopharmaceutical agents currently used for cardiovascular imaging include nuclides such as $^{201}$Tl, $^{99m}$Tc, $^{133}$Xe, $^{11}$C, $^{18}$F, $^{82}$Rb, $^{13}$N, and the like; chelates of nuclides; radiolabeled metabolic agents such as $^{11}$C-deoxy-D-glucose, $^{18}$F-2-fluoro-2-deoxy-D-glucose, [$^{18}$F], [$^{11}$C]- and [$^{123}$I]-β-methyl fatty acid analogs, $^{13}$N-ammonia, and the like; infarct avid agents such as $^{99m}$Tc-tetracycline, $^{99m}$Tc-pyrophosphate, $^{203}$Hg-mercurials, $^{67}$Ga-citrate, and the like; and radiolabeled ligands, proteins, peptides, and monoclonal antibodies.

The present invention provides anticoagulants such as dabigatran and their derivatives as novel radiopharmaceutical agents for cardiovascular imaging, diagnosis and treatment.

SUMMARY OF THE INVENTION

In one embodiment, the present invention provides a direct thrombin inhibitor (DTI) derivative comprising the DTI or a product of the DTI with a PET and a SPECT label.

In one embodiment, the present invention provides a dabigatran DTI derivative or a product of dabigatran.

In one embodiment, the present invention provides a dabigatran DTI derivative or a product of dabigatran DTI derivative with a PET and SPECT label, represented by structure (A):

(A)

wherein R is H, Et, Me, or Bu;
R$_2$ is H, Et, Me, Bu;
n is a number from 2 to 6;
m is a number from 2 to 6;
Z is alkyl, substituted alkyl, alkylene, aryl, or halogen;
Y is alkyl, substituted alkyl, alkylene, aryl, or halogen; and
X is halogen, radiohalogen, chelating moiety or radiolabeled chelating moiety.

According to certain embodiments of the invention, the radiolabel may be selected from the list consisting of $^{131}$I, $^{125}$I, $^{123}$I, $^{124}$I, $^{99m}$Tc, $^{18}$F, $^{68}$Ga, $^{68}$Ga, $^{72}$As, $^{89}$Zr, $^{64}$Cu, $^{62}$Cu, $^{111}$In, $^{203}$Pb, $^{98}$Hg, $^{97}$Ru, $^{11}$C. and $^{201}$Ti.

According to certain embodiments of the invention, the radiolabel is $^{18}$F.

According to certain embodiments of the invention, the radiolabel is $^{123}$I.

According to certain embodiments of the invention, the radiolabel is $^{99m}$Tc.

In one embodiment, the present invention provides a pharmaceutical composition comprising a DTI derivative and a pharmaceutically acceptable carrier.

In another embodiment, the present invention provides a method for providing a positron emission tomography (PET) scan or single photon emission computerized tomography (SPECT) in a subject, comprising:
(a) administering to a subject a DTI derivative; and
(b) imaging gamma rays emitted due to the DTI derivative within said subject to provide a PET or SPECT scan of the DTI derivative contained in said subject.

According to certain embodiments of the invention, the presence, absence or level of the DTI derivative is indicative of atherosclerotic plaque or thrombus in the subject. Targeting plaque formation with DTI for imaging and treatment is rationalized by the fact that both share progress via the inflammation and clotting process.

In another embodiment, the present invention provides a method of treating atherosclerotic plaque or thrombus in a subject, comprising administering to a subject an effective dosage of an unlabeled DTI derivative, whereby the atherosclerotic plaque or thrombus in said subject is treated.

According to certain embodiments of the invention, the method of treating atherosclerotic plaque or thrombus in a subject, comprising administering to a subject an effective dosage of an unlabeled dabigatran DTI derivative, whereby the atherosclerotic plaque or thrombus in said subject is treated.

In one embodiment, the present invention provides a method of providing a dabigatran derivative, comprising the scheme of:

In one embodiment, the present invention provides use of a DTI derivative for the manufacture of an injectable dosage for the in vivo imaging of a subject.

In one embodiment, the present invention provides use of an unlabeled dabigatran DTI derivative for the manufacture of a medicament for the treatment of atherosclerotic plaque or thrombus in a subject.

In one embodiment, the present invention provides a DTI derivative for use in in-vivo imaging of a subject.

In one embodiment, the present invention provides an unlabeled dabigatran DTI derivative for use in treating atherosclerotic plaque or thrombus in a subject.

DETAILED DESCRIPTION

The inventor of the present invention has discovered various compounds useful for cardiovascular imaging, e.g., see U.S. Pat. Nos. 6,299,857; 7,438,891; and 7,060,251.

The present invention provides novel imaging agents derived from anticoagulants, with a label. These novel imaging agents specifically binds and accumulate in actively forming or actively growing plaques or thrombus and therefore are useful for detecting or monitoring plaque formation.

The anticoagulants or derivatives thereof may be used for imaging, diagnosis, prognosis, follow-up of therapy treatment, as well as, treatment of thrombus and plaque formation.

In one embodiment, the invention provides an anticoagulant, its prodrug or a derivative with a radiolabel.

The term "anticoagulant" refers to a class of drugs that work to prevent the coagulation (clotting) of blood. Anticoagulants may be directly or indirectly target thrombin to achieve the anticoagulation effect, as sumarized in Eikelboom and Weitz, 2014, *Circulation*. 2010: 121: 1523-1532, the entirety of which is thereby incorporated by reference. Direct thrombin inhibitors (DTIs) act as anticoagulants by directly inhibiting the enzyme thrombin (factor II). Useful DTIs according to the invention include, but not limited to, Hirudin and derivatives (e.g., Hirudin, Bivalirudin, Lepirudin, Desirudin); univalent DTIs (Argatroban, Melagatran (including its prodrug ximelagatran), Dabigatran (including its prodrug Dabigatran etexilate); and allosteric inhibitors (e.g., DNA aptamers, benzofuran dimers, benzofuran trimers, polymeric lignins).

The anticoagulants according to the present invention may be those oral anticoagulants derived from coumarin such as warfarin (Coumadin) and its salts; heparin and derivative substances such as low molecular weight heparin (LMWH) and ultralow molecular weight heparin and their salts, synthetic pentasaccharide inhibitors of factor Xa such as fondaparinux and idraparinux and their salts; direct factor Xa or IXa inhibitors such as otamixaban, rivaroxaban, apixaban, edoxaban, betrixaban, YM150, TAK442 and RB006 and their salts; direct thrombin inhibitors such as AZD0837, H067637, hirudin, lepirudin, bivalirudin, argatroban and dabigatran and their salts. The term referring to a particular anticoagulant also encompass an organic or inorganic salt of the anticoagulant or its prodrug. For example, the term dabigatran also encompasses dabigatran prodrug debigatran eterxilate. Additional series of anticoagulants involved in steps of the cloting mechanism may also be used according to the present invention.

In one embodiment, the derivative of the present invention comprises a compound having the following structure:

wherein R is H, Et, Me, Bu; $R_2$ is H, Et, Me, Bu; n is a number from 2 to 6; m is a number from 2 to 6; Z is alkyl, substituted alkyl, alkylene, aryl, halogen; Y is alkyl, substituted alkyl, alkylene, aryl, halogen; and X is halogen, radiohalogen, chelating moiety or radiolabeled chelating moiety.

The anticoagulant imaging agents described in the present invention may contain any label in accordance with the invention. Highly specific and sensitive labels are provided by radionuclides, which can then be detected, using positron emission tomography (PET) or Single Photon Emission Computed Tomography (SPECT) imaging. More preferably, the imaging agent of the invention contains a radionuclide selected from the group consisting of $^{131}I$, $^{125}I$, $^{123}I$, $^{99m}Tc$, $^{18}F$, $^{68}Ga$, $^{67}Ga$, $^{72}As$, $^{89}Zr$, $^{64}Cu$, $^{62}Cu$, $^{111}In$, $^{203}Pb$, $^{198}Hg$, $^{11}C$, $^{97}Ru$, and $^{201}Tl$. Such labels may be incorporated into the imaging agent by covalent bonding directly to an atom of the anticoagulant molecule, or the label may be non-covalently or covalently associated with the anticoagulant molecule through a chelating structure or through an auxiliary molecule such as mannitol, gluconate, glucoheptonate, tartrate, and the like. Preferably, the anticoagulant of the present invention directly binds to thrombin or plaque. When a chelating structure is used to provide spatial proximity between the label and the anticoagulant molecule, the chelating structure may be directly associated with the anticoagulant molecule or it may be associated with the anticoagulant molecule through an auxiliary molecule such as mannitol, gluconate, glucoheptonate, tartrate, and the like.

Any suitable chelating structure may be used to provide spatial proximity between the radionuclide and the anticoagulant molecule of the agent through covalent or noncovalent association. Many such chelating structures are known in the art. Preferably, the chelating structure is an $N_2S_2$ structure, an $NS_3$ structure, an $N_4$ structure, an isonitrile-containing structure, a hydrazine containing structure, a HYNIC (hydrazinonicotinic acid) group-containing structure, a 2-methylthiolnicotinic acid group-containing structure, a carboxylate group containing structure, DOTA and the like. In some cases, chelation can be achieved without including a separate chelating structure, because the radionuclide chelates directly to atom(s) in the anticoagulant, for example to oxygen or nitrogen contained atoms and other electron donors and acceptors in various anticoagulants.

The chelating structure, auxiliary molecule, or radionuclide may be placed in spatial proximity to any position of the anticoagulant molecule which does not interfere with the interaction of the anticoagulant molecule with its target site in cardiovascular tissue. Accordingly, the chelating structure, auxiliary molecule, or radionuclide may be covalently or non-covalently associated with any moiety of the anticoagulant molecule except the receptor-binding moiety.

Radionuclides may be part of the molecule as a radiolabel and/or placed in spatial proximity to the anticoagulant molecule using known procedures which effect or optimize bonding, association, or attachment of the specific radionuclide. For example, when $^{123}I$ is the radionuclide, the imaging agent may be labeled in accordance with the known radioiodination procedures such as direct radioiodination with chloramine T, radioiodination exchange for a halogen or an organometallic group, and the like. When the radionuclide is $^{99m}Tc$, the imaging agent may be labeled using any method suitable for attaching $^{99m}TC$ to a ligand molecule. Preferably, when the radionuclide is $^{99m}Tc$, an auxiliary molecule such as mannitol, gluconate, glucoheptonate, or tartrate is included in the labeling reaction mixture, with or without a chelating structure. More preferably, $^{99m}Tc$ is placed in spatial proximity to the anticoagulant molecule by reducing $^{99m}TcO_4$ with tin in the presence of mannitol and the anticoagulant molecule. Other reducing agents, including tin tartrate or non-tin reductants such as sodium dithionite, or other methods for chelating $^{99m}Tc$ may also be used to make the cardiovascular imaging agent of the invention.

In general, labeling methodologies vary with the choice of radionuclide, the moiety to be labeled and the clinical condition under investigation. Labeling methods using 99mTc and 111 In are described for example in Peters, A. M. et al., Lancet 2: 946-949 (1986); Srivastava, S. C. et al., Semin. Nucl. Med. 14(2):68-82 (1984); Sinn, H. et al., Nucl. Med. (Stuttgart) 13:180, 1984; McAfee, J. G. et al., J. Nucl. Med. 17:480-487, 1976; McAfee, J. G. et al., J. Nucl. Med. 17:480-487, 1976; Welch, M. J. et al., J. Nucl. Med. 18:558-562, 1977; McAfee, J. G., et al., Semin. Nucl. Med. 14(2): 83, 1984; Thakur, M. L., et al., Semin. Nucl. Med. 14(2): 107, 1984; Danpure, H. J. et al., Br. J. Radiol., 54:597-601, 1981; Danpure, H. J. et al., Br. J. Radiol. 55:247-249, 1982; Peters, A. M. et al., J. Nucl. Med. 24:39-44, 1982; Gunter, K. P. et al., Radiology 149:563-566, 1983; and Thakur, M. L. et al., J. Nucl. Med. 26:518-523, 1985; Benerjee et al., Semin Nucl Med., 31(4):260-77, 2001.

After the labeling reaction is complete, the reaction mixture may optionally be purified using one or more chromatography steps such as Sep Pack or high performance liquid chromatography (HPLC). Any suitable HPLC system may be used if a purification step is performed, and the yield of cardiovascular imaging agent obtained from the HPLC step may be optimized by varying the parameters of the HPLC system, as is known in the art. Any HPLC parameter may be varied to optimize the yield of the cardiovascular imaging agent of the invention. For example, the Ph may be varied, e.g., raised to decrease the elution time of the peak corresponding to the cardiovascular imaging agent of the invention. Recent methods allow automation of the radiolabeling methods especially for short lived radiolnuclides. For example radiofluorination of an appropriate precursor may be automated on GE FastLab system.

The labeled anticoagulants may be used for imaging to measure direct physiological parameters as an indictor of treatment efficacy. They may be used for vascular imaging, e.g., in a more efficient manner.

Dabigatran (Pradaxa in Australia, Europe, USA and Canada (previously was Pradax in Canada, name changed to Pradaxa as of January 2013), Prazaxa in Japan) is an oral anticoagulant drug that acts as a direct thrombin (factor IIa) inhibitor. It was developed by the pharmaceutical company Boehringer Ingelheim.

Dabigatran's prodrug debigatran eterxilate, with a chemical name of Ethyl 3-{[(2-{[(4-{N'-hexyloxycarbonyl carbamimidoyl}phenyl)amino]methyl}-1-methyl-1H-benz-imidazol-5-yl)carbonyl] (pyridin-2-yl-amino)propanoate, is an anticoagulanet that acts as a direct thrombin (factor IIa) inhibitor. Ingested orally, debigatran eterxilate is split in the liver and the blood plasma by hydrolysis to form the active dabigatran.

Dabigatran is a competitive and reversible direct thrombin inhibitor. Thrombin is first synthesized as prothrombin (coagulation factor II) which is proteolytically cleaved to form thrombin in the coagulation cascade, which ultimately results in the reduction of blood loss. Thrombin acts as a serine protease that converts soluble fibrinogen into insoluble strands of fibrin, as well as catalyzing many other coagulation-related reactions.

Thrombin plays a role in the last step of blood coagulation, being composed of one active site and two secondary binding exosites. The first exosite aids active site binding through docking substrates such as fibrin, whilst the second binds heparin. Dabigatran thus inactivates both fibrin-bound and free thrombin through binding to the active site; proving more effective than indirect thrombin inhibitors such as unfractionated heparin (which cannot inhibit fibrin-bound thrombin).

Dabigatran may be radiolabeled with nuclides such as $^{131}I$, $^{125}I$, $^{123}I$, $^{124}I$, $^{99m}Tc$, $^{18}F$, $^{68}Ga$, $^{67}Ga$, $^{72}As$, $^{89}Zr$, $^{64}Cu$, $^{62}Cu$, $^{111}In$, $^{203}Pb$, $^{98}Hg$, $^{97}Ru$, $^{11}C$ and $^{201}Ti$ for PET and SPECT imaging.

Particularly preferred radionuclides agents have an appropriate half-life and high specific activity for the desired imaging.

In one embodiment, the inventor has developed an F-18 analog of an anticoagulant (e.g., Dabigatran (Pradaxa) that will be used as a PET imaging tracer of thrombus and plaque formation in the cardiovascular system. In another embodiment, the inventor has discovered that anticoagulant such as radilabeled dabigatran, and derivatives thereof, of the present invention may be useful for early diagnosis and follow-up of treatment of cardiovascular disease, and potentially other specific forms of thrombus fomation due gentic diseases and pre- and post-operations.

According to some embodiments of the present invention, the radiolabeled compounds provide imaging insight, pre and post treatment in patients undergoing stenting, bloon catheterization, neovascularization and transplant related intervention.

In other embodiments the present disclosure relates to compounds and methods for radiolabel drugs for use as in vivo imaging biomarker. These specific compounds target the blood clotting chain, plaque formation and inflammation associated with the formation of these clinical disorders. In another embodiments these biomarkers are used for direct assessment of tissue damage. In other embodiments these radiolabeled compounds are used for following the efficacy of drug treatment of vascular diseases, such as inflammatory processes, atheromas, atherosclerosis and the blood cloting casscade.

In one embodiment, onr or more anticoagulant drugs, fibrinolytic drugs and anti-platelet drugs are labeled according to the present invention and used for prevention treatment of thrombus and plaque formation. Examples of such drugs are described in Weitz J I, Hirsh J, Samama M M, American College of Chest Physicians. New antithrombotic drugs: American College of Chest Physicians Evidence-Based Clinical Practice Guidelines (8th Edition). Chest 2008; 133:234S; Franchini M, Mannucci P M. New anticoagulants in internal medicine: an update. Eur J Intern Med 2010; 21:466; The Sixth (2000) ACCP guidelines for antithrombotic therapy for prevention and treatment of thrombosis. Chest 2001; 119 (Supplement, January, 2001), each of which is incorporated herein by its entirety.

Anticoagulant drugs include but are not limited to:

Heparin. Heparin is an intravenous drug that has an immediate (within seconds) inhibitory effect on the clotting factors. Doctors can adjust its dosage frequently, as needed, following the partial thromboplastin time (PTT) blood test. The PTT reflects how much the clotting factors have been inhibited. (That is, it reflects the "thinness" of the blood.) Heparin is used exclusively in hospitalized patients.

Low Molecular Weight Heparin: enoxaparin (Lovenox), dalteparin (Fragmin). These drugs are purified derivatives of heparin. Their major advantages are that they can be given as skin injections (which almost anyone can learn to do in a few minutes) and do not need to be closely monitored with blood tests. So, unlike heparin, they can be administered with relative safety on an outpatient basis.

Newer Intravenous or Subcutaneously-Administered Anticoagulant Drugs. Several "heparin-like" anticoagulant drugs have been developed, including argatroban, bivalirudin (Angiomax), fondaparinux (Arixtra) and lepirudin (Refludan). The optimal time and place to use all of these drugs are being slowly worked out.

Warfarin (Coumadin). Until recently, Coumadin was the only orally administered anticoagulant drug available. The biggest problem with Coumadin has been in adjusting its dosage. When first taken, Coumadin's dosage must be stabilized over a period of weeks with frequent blood tests (the INR blood test). Even after stabilization the INR still needs to be monitored periodically and the dosage often re-adjusted. So, getting to and maintaining the "right" dose of Coumadin has always been difficult and inconvenient.

Dabigatran (Pradaxa) and Other "New" Oral Anticoagulant Drugs. Because the dose of warfarin can be relatively difficult to regulate, drug companies have worked for years to come up with "warfarin-substitutes." Dabigatran was the first of these new anticoagulants to be approved by the U.S. Food and Drug Administration. (Rivaroxaban and apixaban are two similar drugs that are just now reaching the market.) The chief advantage of all these drugs is that they can be given in fixed daily dosages and do not require blood tests or dosage adjustments.

Fibrinolytic Drugs include but are not limited to:

Streptokinase, urokinase, alteplase, reteplase, tenecteplase. These powerful drugs are given acutely and intravenously to dissolve blood clots that are in the process of forming. For the most part their use is limited to patients who are within the first few hours of an acute heart attack or stroke, to attempt to re-open a blocked artery and prevent permanent tissue damage. They can be tricky to use and carry a substantial risk of bleeding complications. However, in the right circumstances the use of these drugs can prevent death or disability. Of these drugs, streptokinase is the most frequently used fibrinolytic drug world-wide because it is relatively cheap. In the United States, tenecteplase is currently the drug of choice because it appears to cause fewer disastrous bleeding consequences and is easier to administer than the other drugs.

Anti-platelet drugs include but are not limited to:

Aspirin and diypyramidole (Aggrenox). These drugs have a modest effect on platelet "stickiness" but have fewer bleeding-related side effects than the other anti-platelet drugs. They are often used in an attempt to reduce the risk of heart attack or stroke in people whose risk is elevated.

Ticlopidine (Ticlid), clopidrogel (Plavix) and prasugrel (Efflent). These drugs are more powerful (and therefore riskier) than the first group. They are commonly used when the risk of arterial clotting is especially high. Their most common application is in people who have received coronary artery stents. Here, decisions about when and how long to use them have become controversial.

IIb/IIIa Inhibitors: abciximab (ReoPro), eptifabitide (Integrilin), tirofiban (Aggrastat). The IIb/IIIa inhibitors are the most powerful group of platelet inhibitors. They inhibit a receptor on the surface of platelets (the so-called IIb/IIIa receptor) that is essential for platelet stickiness. Their chief usage is to prevent acute clotting after interventional procedures (such as angioplasty and stent placement) and in patients with acute coronary artery syndrome. These drugs are very expensive and (in general) must be given intravenously.

In one embodiment, Pradaxa, Warferin, low molecular weight heparin and 5-oligo-sugars were evaluated in animals and human, and are used for prevention treatment of thrombus and plaque formation.

Specific nuclides forms of dabigatran derivatives (radiolabeled, fluorinated or radiofluorinated) are used to target and treat specific vascular disease as imaging biomarkers of clot formation and other vascular disease. Dabigatran (Pradaxa) is a more specific drug as clot imaging biomarker when radiolabeled or attached to a paramagnetic contrast.

In a more specific embodiment, $^{18}F$ derivatives of Dabigatran are used as agents for direct imaging of thrombus and plaque formation.

Dabigatran etexilate mesylate; N-[[2-[[[4-[[[(Hexyloxy)carbonyl]amino]iminomethyl]phenyl]amino]methyl]-1-methyl-1H-benzimidazol-5-yl]carbonyl]-N-2-pyridinyl-beta-alanine ethyl ester monomethanesulfonat.

[18]F-dabigatran is prepared according to the following route according to one embodiment of the invention. The following precursor and radiolabeling synthesis are novel is different from the present Dabigatran (Pradaxa) active drug synthesis.

Synthesis

Figure 1:
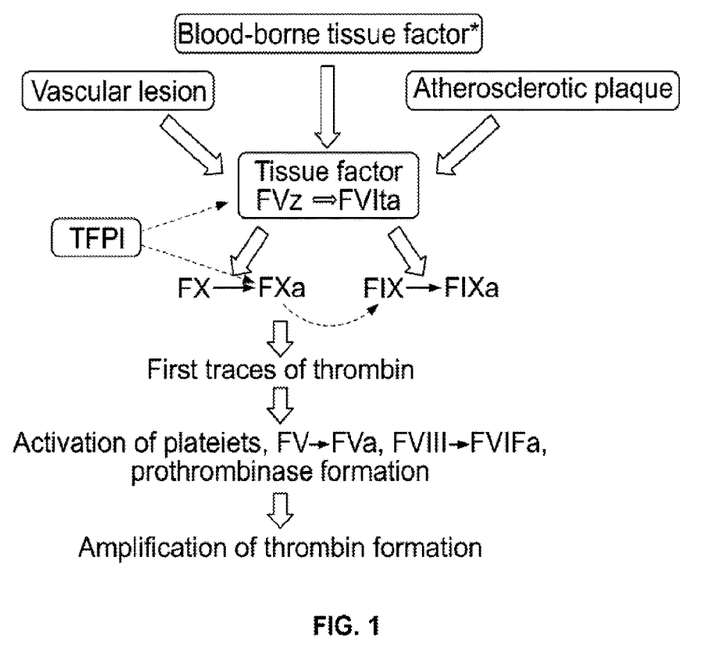
FIG. 1. Mechanism of Action of dabigatran: direct binding to thrombin according to one embodiment of the invention.

The clotting chain of thrombin formation is depicted in FIG. 1.

Figure 2:
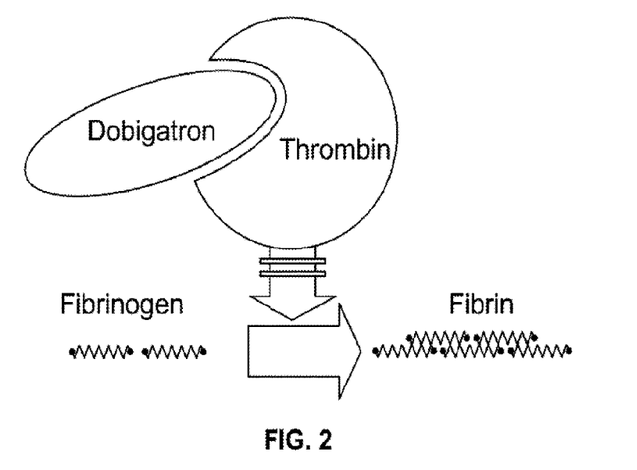
FIG. 2. The direct binding of dabigatran to thrombin leads to direct imaging of clot formation according to one embodiment of the invention.
Figure 3:
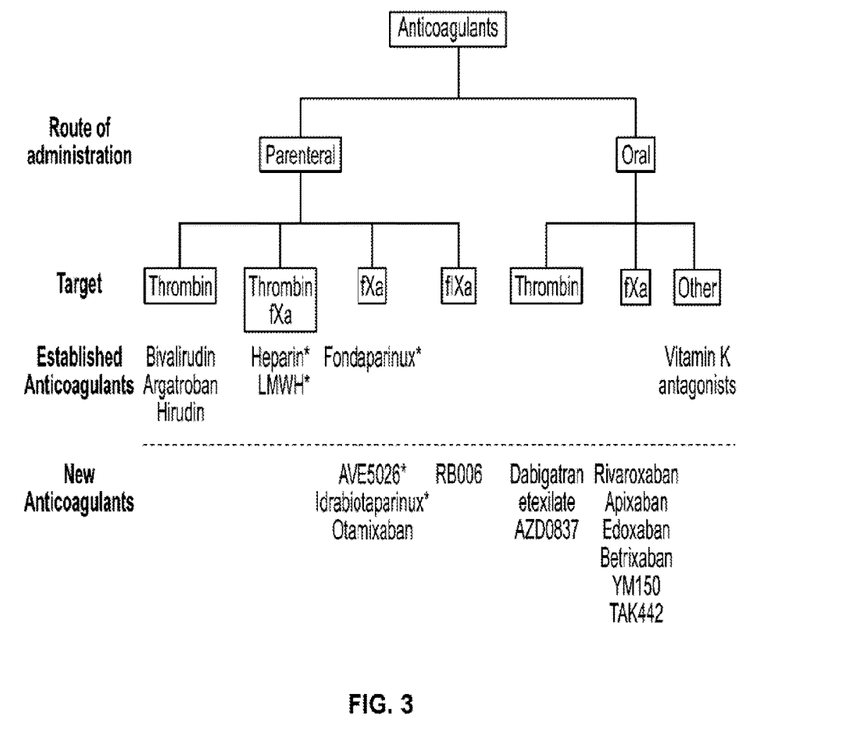
FIG. 3. Figure adopted from Eikelboom and Weitz, 2014, *Circulation*. 2010: 121: 1523-1532, summarizing various anticoagulants according to one embodiment of the invention.

Pradaxa mechanism of action is a direct binding to thrombin as shown in FIG. 2.

According to some embodiment, the direct binding to thrombin by dabigatran enables a PET radiolabeled dabigatran derivative to directly image clot formation for diagnosis and monitoring drug efficacy.

In other embodiments, the direct binding to thrombin by dabigatran enables a PET radiolabeled dabigatran derivative to follow the treatment of clotting disorders and of treatment with dabigatran.

In another aspect, the anticoagulants and derivatives thereof are provided in the form of a pharmaceutically appropriate dosage of one or more of the anticoagulants and their derivatives described and claimed herein formulated with a pharmaceutically acceptable carrier.

As can be appreciated, the anticoagulants and their derivatives of the invention are useful for imaging in other modalities in addition to PET imaging. In yet another aspect of the invention, a method for providing a positron emission tomography (PET) scan of a subject is provided. Such a method includes steps of: (a) administering to a subject an anticoagulant and derivative thereof containing an $^{18}F$ label as described and claimed herein; and (b) imaging gamma rays emitted due to the compound within the subject in order to provide a PET scan of the compound contained in the subject.

In yet another aspect of the invention, a method for providing a Single photon emission computerized tomography (SPECT) scan of a subject is provided. Such a method includes steps of: (a) administering to a subject an anticoagulant and derivative thereof containing an $^{123}I$ or $^{99m}Tc$ label as described and claimed herein; and (b) imaging gamma rays emitted due to the compound within the subject in order to provide a SPECT scan of the compound contained in the subject.

In certain embodiments, the presence, absence or level of the anticoagulant and derivative thereof within the subject is indicative of a disease state including, but not limited to, atherosclerotic plaque alternatively present in the heart, brain, carotid artery or other blood vessels of the subject.

The subject is preferably a living animal, most preferably a human.

The anticoagulant and derivative thereof is typically administered to the subject via parenteral injection, preferably intravenous injection.

The invention further encompasses treatment methods, including treatment of atherosclerotic plaque in a subject. Such a method includes steps of administering to a subject an effective dosage of an $^{19}F$ (cold fluorine) anticoagulant derivatives thereof of the invention, whereby the atherosclerotic plaque is treated in the subject.

The invention also contemplates the use of an anticoagulant and derivative thereof as described and claimed herein for the manufacture of an injectable dosage for the in vivo imaging of a subject as well as a medicament for the treatment of disease conditions such as atherosclerotic plaque. In addition, the invention encompasses the use of the present compounds in vivo imaging of a subject and treatment of clotting conditions.

In certain aspects, the invention is directed to radiolabeled anticoagulants (e.g., dabigatran) and their derivatives for medical imaging of inflammatory sites such as atherosclerotic plaques in the heart, brain, carotid artery or other blood vessels of a subject. In other aspects, the anticoagulants $^{19}F$ derivatives (e.g., dabigatran) as unlabeled form are treatment agents for various disease conditions including, e.g., atherosclerotic plaques and other clotting disease.

The invention further provides methods for the preparation and use of the anticoagulants (e.g., dabigatran) and their derivatives for anticoagulant and treating active infection and other inflammatory processes, such as atherosclerosis.

As can be appreciated, the anticoagulants (e.g., dabigatran) and their derivatives of the present invention may be used for several purposes. For instance, the described anticoagulant (e.g., radiolabeled, fluorinated or radiofluorinated dabigatran derivatives) are a potential research tool for animal studies; a diagnosis agent for clinicians; a biomarker for biology studies; a potential class of drugs to treat atherosclerosis or other clotting Disease; a SPECT probe for atherosclerosis or other diseases; and a PET probe for atherosclerosis or other disease diagnosis.

Anticoagulants (e.g., radiolabeled, fluorinated or radiofluorinated dabigatran derivatives) are expected to be beneficial for use in the imaging methods of the invention.

Anticoagulants (e.g., radiolabeled, fluorinated or radiofluorinated dabigatran derivatives) that exhibit improved imaging qualities are preferred.

Anticoagulants (e.g., radiolabeled, fluorinated or radiofluorinated dabigatran derivatives) lacking radiolabel are, of course, useful for the treatment methods claimed and disclosed herein.

In certain embodiments directed to formulations and medicaments for disease treatment including, e.g., atherosclerosis, the inventive anticoagulants (e.g., radiolabeled, fluorinated or radiofluorinated dabigatran derivatives) may be provided as pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

The inventive anticoagulants (e.g., radiolabeled, fluorinated or radiofluorinated dabigatran derivative) further encompass esters thereof, wherein the acidic hydrogen on one or more of the acidic moieties is substituted by an alkyl group.

Where the anticoagulants (e.g., radiolabeled, fluorinated or radiofluorinated dabigatran derivatives) according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The anticoagulants (e.g., radiolabeled, fluorinated or radiofluorinated dabigatran derivatives) of the present invention are particularly useful when formulated in the form of a pharmaceutical injectable dosage, including a compound described and claimed herein in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The anticoagulants (e.g., dabigatran) and their derivatives according to the present invention are anticipated to act as treatment agents for inflammation, particularly atherosclerotic plaques, as can be demonstrated by standard protocols commonly known in the field. Accordingly, another aspect of the invention provides a method for treating atherosclerotic plaque in a subject, comprising administering to a subject an effective dosage of a compound according to the present invention, whereby the atherosclerotic plaque is treated in the subject. In the treatment of atherosclerotic plaque, suitable dosage level (i.e, an effective amount) is from about 0.001 mg/kg to about 500 mg/kg per day, preferably about 1 mg/kg per day. The anticoagulants (e.g., dabigatran) and their derivatives may be administered on a regimen of 1 to 4 times per day, or on a continuous basis.

The invention as embodied in a kit for imaging comprises one or more of the imaging agents described above, in combination with a pharmaceutically acceptable carrier such as human serum albumin. Human serum albumin for use in the kit of the invention may be made in any way, for example, through purification of the protein from human serum or though recombinant expression of a vector containing a gene encoding human serum albumin. Other substances may also be used as carriers in accordance with this embodiment of the invention, for example, detergents, dilute alcohols, carbohydrates, auxiliary molecules, and the like. The kit of the invention may of course also contain such other items as may facilitate its use, such as syringes, instructions, reaction vials, and the like.

In one embodiment, a kit according to the invention contains from about 1 to about 30 mCi of the radionuclide-labeled cardiovascular imaging agent described above, in combination with a pharmaceutically acceptable carrier. The cardiovascular imaging agent and carrier may be provided in solution or in lyophilized form. When the cardiovascular imaging agent and carrier of the kit are in lyophilized form, the kit may optionally contain a sterile and physiologically acceptable reconstitution medium such as water, saline, buffered saline, and the like.

In another embodiment, the kit of the invention may contain the unlabeled anticoagulant precursor for radiolabeling with a PET and aSPECT radionuclides. In another embodiment, the kit of the invention may contain the unlabeled anticoagulant molecule which has been covalently or non-covalently combined with a chelating agent; an auxiliary molecule such as mannitol, gluconate, glucoheptonate, tartrate, and the like; and a reducing agent such as $SnCl_2$ or tin tartrate. The unlabeled anticoagulant molecule/chelating agent and the auxiliary molecule may be present as separate components of the kit or they may be combined into one kit component. The unlabeled anticoagulant molecule/chelating agent, the auxiliary molecule, and the reducing agent may be provided in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

Determination and optimization of such stabilizers and stabilization methods are well within the level of skill in the art. When the unlabeled anticoagulant molecule/chelating, agent of this embodiment are in lyophilized form, the kit may optionally contain a sterile and physiologically acceptable reconstitution medium such as water, saline, buffered saline, and the like. The amounts of unlabeled anticoagulant molecule/chelating agent, auxiliary molecule, and reducing agent in this embodiment can be optimized in accordance with the methods for making the cardiovascular imaging agent set forth above. Radionuclides, including, but not limited to, $^{99m}Tc$, e.g. obtained from a commercially available $^{99}Mo/^{99m}Tc$ generator or commercially available $^{123}I$, may be combined with the unlabeled anticoagulant molecule/chelating agent and the reducing agent for a sufficient period of time and at a temperature sufficient to chelate the radionuclide to the anticoagulant molecule/chelating agent, and the imaging agent thus formed is injected into the patient.

The cardiovascular imaging agents of the invention may be used in accordance with the methods of the invention by those of skill in the art, e.g., by specialists in nuclear medicine, to image plaque in the cardiovascular system of a subject. Images are generated by virtue of differences in the spatial distribution of the imaging agents which accumulate in the various tissues and organs of the subject. The spatial distribution of the imaging agent accumulated may be measured using any suitable means, for example, a PET or a SPECT Camara, and the like. Some cardiovascular lesions may be evident when a less intense spot appears within the image, indicating the presence of tissue in which a lower concentration of imaging agent accumulates relative to the concentration of imaging agent which accumulates in surrounding cardiovascular tissue. Alternatively, a cardiovascular lesion might be detectable as a more intense spot within the image, indicating a region of enhanced concentration of the imaging agent at the site of the lesion relative to the concentration of agent which accumulates in surrounding cardiovascular tissue. Thrombi and embolisms are examples of cardiovascular lesions which accumulate enhanced concentrations of the imaging agents of the invention. Accumulation of lower or higher amounts of the imaging at the site of a lesion may readily be detected visually, by inspection of the image of the cardiovascular tissue. Alternatively, the extent of accumulation of the imaging agent may be quantified using known methods for quantifying radioactive emissions. A particularly useful imaging approach employs more than one imaging agent to perform simultaneous studies. For example, simultaneous studies of perfusion and metabolic function would allow study of coupling and uncoupling of flow of metabolism, thus facilitating determinations of tissue viability after a cardiac injury. Such determinations are useful in diagnosis of cardiac ischemia, cardiomyopathy, tissue viability, hibernating heart, and other heart abnormalities.

An effective amount of an imaging agent comprising at least one anticoagulant molecule and a label (e.g. from about 1 to about 50 mCi of a radionuclide) may be combined with a pharmaceutically acceptable carrier for use in imaging studies. In accordance with the invention, "an effective amount" of the imaging agent of the invention is defined as an amount sufficient to yield an acceptable image using equipment which is available for clinical use. An effective amount of the imaging agent of the invention may be administered in more than one injection. Effective amounts of the imaging agent of the invention will vary according to factors such as the degree of susceptibility of the individual, the age, sex, and weight of the individual, idiosyncratic responses of the individual, the dosimetry. Effective amounts of the imaging agent of the invention will also vary according to instrument and film-related factors. Optimization of such factors is well within the level of skill in the art.

"Pharmaceutically acceptable" as used herein means that the compound or composition or carrier is suitable for administration to a subject to achieve the imaging or treatment described herein, without unduly deleterious side effects in light of the necessity of the imaging or treatment.

As used herein, "pharmaceutically acceptable carrier" includes any and all solvents, dispersion media, coatings, antibacterial and antifungal agents, isotonic agents, absorption delaying agents, and the like. The formulation used in the present invention may also contain stabilizers, preservatives, buffers, antioxidants, or other additives known to those of skill in the art. The use of such media and agents for pharmaceutically active substances is well known in the art. Supplementary active compounds can also be incorporated into the imaging agent or the invention. The imaging agent of the invention may further be administered to an individual in an appropriate diluent or adjuvant, co-administered with enzyme inhibitors or in an appropriate carrier such as human serum albumin or liposomes. Pharmaceutically acceptable diluents include sterile saline and other aqueous buffer solutions. Adjuvants contemplated herein include resorcinols, non-ionic surfactants such as polyoxyethylene oleyl ether and n-hexadecyl polyethylene ether. Enzyme inhibitors include pancreatic trypsin inhibitor, diethylpyrocarbonate, and trasylol. Liposomes inhibitors include water-in-oil-in-water CGF emulsions as well as conventional liposomes (Strejan et al., J Neuroimmunol 7:27 [1984]).

The subject imaging agents can be administered to a subject in accordance with any means that facilitates accumulation of the agent in a subject's cardiovascular system. Preferably, the imaging agent of the invention is administered by arterial or venous injection, and has been formulated as a sterile, pyrogen-free, parenterally acceptable aqueous solution. The preparation of such parenterally acceptable solutions, having due regard to pH, isotonicity, stability, and the like, is within the skill in the art. A preferred formulation for intravenous injection should contain, in addition to the cardiovascular imaging agent, an isotonic vehicle such as Sodium Chloride Injection, Ringer's Injection, Dextrose Injection, Dextrose and Sodium Chloride Injection, Lactated Ringer's Injection, or other vehicle as known in the art.

The amount of imaging agent used for diagnostic purposes and the duration of the imaging study will depend upon the nature and severity of the condition being treated, on the nature of therapeutic treatments which the patient has undergone, and on the idiosyncratic responses of the patient. Ultimately, the attending physician will decide the amount of imaging agent to administer to each individual patient and the duration of the imaging study.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are herein described. All publications mentioned herein are hereby incorporated by reference in their entirety for the purpose of describing and disclosing the materials and methodologies that are reported in the publication which might be used in connection with the invention.

What is claimed is:

1. A dabigatran DTI derivative or a product of dabigatran DTI derivative with a PET or SPECT radiolabel, represented by structure (A):

(A)

wherein R is H, Et, Me, or Bu;
R$_2$ is H, Et, Me, or Bu;
n is a number from 2 to 6;
m is a number from 2 to 6;
Z is alkyl, substituted alkyl, alkylene, aryl, or halogen;
Y is alkyl, substituted alkyl, alkylene, aryl, or halogen; and
X is halogen, radiohalogen, chelating moiety or radiolabeled chelating moiety.

2. The DTI derivative according to claim 1, wherein said radiolabel is selected from the group consisting of $^{131}$I, $^{125}$I, $^{123}$I, $^{124}$I, $^{99m}$Tc, $^{18}$F, $^{68}$Ga, $^{67}$Ga, $^{72}$As, $^{89}$Zr, $^{64}$Cu, $^{62}$Cu, $^{111}$In, $^{203}$Pb, $^{98}$Hg, $^{97}$Ru, $^{11}$C and $^{201}$Ti.

3. The DTI derivative according to claim 1, wherein said radiolabel is $^{18}$F.

4. The DTI derivative according to claim 1, wherein said radiolabel is $^{123}$I.

5. The DTI derivative according to claim 1, wherein said radiolabel is $^{99m}$Tc.

6. A pharmaceutical composition, comprising the DTI derivative according to claim 1 and a pharmaceutically acceptable carrier.

7. A method for providing a positron emission tomography (PET) scan or single photon emission computerized tomography (SPECT) in a subject, comprising:
(a) administering to said subject the radiolabeled dabigatran DTI derivative according to claim 1; and
(b) imaging gamma rays emitted due to the DTI derivative within said subject to provide a PET or SPECT scan of the DTI derivative contained in said subject.

8. The method according to claim 7, wherein the presence, absence or level of said DTI derivative is indicative of the presence or absence of atherosclerotic plaque or thrombus in said subject.

9. A method of treating atherosclerotic plaque or thrombus in a subject, comprising administering to said subject an effective dosage of the dabigatran DTI derivative of claim 1, whereby the atherosclerotic plaque or thrombus in said subject is treated.

10. A method of treating atherosclerotic plaque or thrombus in a subject, comprising: administering to said subject an effective dosage of the dabigatran DTI derivative of claim 1; and imaging said subject to determine the presence or absence of atherosclerotic plaque or thrombus in said subject, whereby the atherosclerotic plaque or thrombus in said subject is treated.

11. A method for manufacturing an injectable dosage for the in vivo imaging of a subject, the method comprising: providing the dabigatran DTI derivative of claim 1.

12. A method for manufacturing a medicament for the treatment of atherosclerotic plaque or thrombus in a subject, the method comprising: providing the dabigatran DTI derivative of claim 1.

13. A DTI derivative according to claim 1 for use in in-vivo imaging of a subject.

* * * * *